United States Patent
Shen et al.

(10) Patent No.: US 10,438,057 B2
(45) Date of Patent: Oct. 8, 2019

(54) SKIN CARE EVALUATION METHOD AND ELECTRONIC DEVICE THEREOF

(71) Applicant: CAL-COMP BIG DATA, INC., New Taipei (TW)

(72) Inventors: Shyh-Yong Shen, New Taipei (TW); Min-Chang Chi, New Taipei (TW); Yung-Hsuan Lin, New Taipei (TW); Ching-Wei Wang, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 198 days.

(21) Appl. No.: 15/641,351

(22) Filed: Jul. 5, 2017

(65) Prior Publication Data
US 2018/0357471 A1    Dec. 13, 2018

(30) Foreign Application Priority Data
Jun. 9, 2017    (CN) .......................... 2017 1 0430937

(51) Int. Cl.
*G06K 9/00* (2006.01)
*A61B 5/00* (2006.01)
(Continued)

(52) U.S. Cl.
CPC .......... *G06K 9/00335* (2013.01); *A61B 5/441* (2013.01); *A61B 5/442* (2013.01);
(Continued)

(58) Field of Classification Search
CPC .......... G06K 9/00255; G06K 9/00175; G06K 9/00335; G06K 9/6202; G06K 9/628;
(Continued)

(56) References Cited

U.S. PATENT DOCUMENTS

| | | | |
|---|---|---|---|
| 8,238,623 B2 * | 8/2012 | Stephan ................. | A61B 5/442 382/100 |
| 8,437,540 B2 * | 5/2013 | Stephan ................ | G06T 7/0012 382/162 |

(Continued)

OTHER PUBLICATIONS

"Search Report of Europe Counterpart Application", dated May 24, 2018, p. 1-p. 12.

*Primary Examiner* — Katrina R Fujita
(74) *Attorney, Agent, or Firm* — JCIPRNET

(57) ABSTRACT

A skin care evaluation method, which is adapted for an electronic device to evaluate a skin care procedure including a plurality of skin care behaviors. The skin care evaluation method includes following steps. A plurality of image information is sequentially captured at a plurality of image capturing time. A plurality of user actions corresponding to the image information is analyzed, where a plurality of consecutive image information of the image information corresponds to one of the user actions. The image information is classified to the skin care behaviors according to the user action corresponding to each of the image information. Each of the skin care behaviors corresponds to a plurality of the user actions. A duration of each of the skin care behaviors is calculated according to the image capturing time of the image information classified to each of the skin care behaviors. An electronic device using the skin care evaluation method is also provided.

4 Claims, 2 Drawing Sheets

(51) Int. Cl.
  *G16H 30/40* (2018.01)
  *G16H 20/00* (2018.01)
  *G06K 9/62* (2006.01)
  *G16H 50/70* (2018.01)

(52) U.S. Cl.
  CPC ..... *G06K 9/00255* (2013.01); *G06K 9/00275* (2013.01); *G06K 9/6202* (2013.01); *G06K 9/628* (2013.01); *G16H 20/00* (2018.01); *G16H 30/40* (2018.01); *G06T 2207/30088* (2013.01); *G16H 50/70* (2018.01)

(58) Field of Classification Search
  CPC ........ G16H 20/00; G16H 30/40; G16H 50/70; G06T 2207/30088; A61B 5/441; A61B 5/442
  See application file for complete search history.

(56) References Cited

U.S. PATENT DOCUMENTS

| | | | | |
|---|---|---|---|---|
| 9,668,653 | B2* | 6/2017 | Qu | A61B 5/0082 |
| 9,789,295 | B2* | 10/2017 | Zhou | A61B 5/4836 |
| 9,955,909 | B2* | 5/2018 | Flament | A61B 5/0077 |
| 2002/0090123 | A1* | 7/2002 | Bazin | A45D 44/005 |
| | | | | 382/128 |
| 2003/0063801 | A1* | 4/2003 | Rubinstenn | A45D 44/005 |
| | | | | 382/190 |
| 2003/0065278 | A1* | 4/2003 | Rubinstenn | A45D 44/005 |
| | | | | 600/587 |
| 2007/0040907 | A1* | 2/2007 | Kern | A61B 5/0059 |
| | | | | 348/77 |
| 2009/0245603 | A1* | 10/2009 | Koruga | A45D 44/00 |
| | | | | 382/128 |
| 2010/0185064 | A1* | 7/2010 | Bandic | A61B 5/0059 |
| | | | | 600/306 |
| 2011/0054354 | A1* | 3/2011 | Hunter | A01G 7/00 |
| | | | | 600/587 |
| 2011/0160563 | A1* | 6/2011 | Glogau | A61B 5/055 |
| | | | | 600/410 |
| 2011/0301441 | A1* | 12/2011 | Bandic | A61B 5/0059 |
| | | | | 600/306 |
| 2012/0300996 | A1* | 11/2012 | Nakamura | G06K 9/0014 |
| | | | | 382/128 |
| 2012/0321759 | A1* | 12/2012 | Marinkovich | A61B 5/0531 |
| | | | | 426/231 |
| 2014/0275948 | A1* | 9/2014 | Kamisoyama | A61B 5/6898 |
| | | | | 600/407 |
| 2015/0099947 | A1* | 4/2015 | Qu | A61B 5/442 |
| | | | | 600/306 |
| 2015/0160730 | A1 | 6/2015 | Bei | |
| 2015/0346936 | A1 | 12/2015 | Rodan et al. | |
| 2016/0063312 | A1* | 3/2016 | Hara | A61B 5/0077 |
| | | | | 382/103 |
| 2016/0224825 | A1* | 8/2016 | Tomita | G06K 9/00268 |
| 2017/0061609 | A1* | 3/2017 | Son | A61B 5/441 |

* cited by examiner

SKIN CARE EVALUATION METHOD AND ELECTRONIC DEVICE THEREOF

CROSS-REFERENCE TO RELATED APPLICATION

This application claims the priority benefit of China Applications serial no. 201710430937.6, filed on Jun. 9, 2017. The entirety of the above-mentioned patent application is hereby incorporated by reference herein and made a part of this specification.

BACKGROUND OF THE INVENTION

Field of the Invention

The invention relates to an image analysis method and an electronic device, and particularly relates to a skin care evaluation method and an electronic device thereof.

Description of Related Art

Regardless of office worker or diligent housewife, skin care is one of the indispensable procedures for modern people every day. Generally, the skin care at least includes three main steps, i.e. cleaning, basic moisturizing and sun screening, and for people with a specific requirement or a specific skin type, more complicated procedures are probably included.

However, due to reasons such as laziness, busy or other special reasons, many people will miss out on the procedure for skin care, or a care action is inadequate due to haste, which results in a poor skin care effect.

SUMMARY OF THE INVENTION

The invention is directed to a skin care evaluation method, by which by analyzing a plurality of images captured during skin care, it is able to evaluate whether a skin care procedure is adequate and indeed.

The invention provides a skin care evaluation method, which is adapted for an electronic device to evaluate a skin care procedure including a plurality of skin care behaviours. The skin care evaluation method includes following steps. A plurality of image information is sequentially captured at a plurality of image capturing time. A plurality of user actions corresponding to the image information is analyzed, where a plurality of consecutive image information of the image information corresponds to one of the user actions. The image information is classified to the skin care behaviours according to the user action corresponding to each of the image information. Each of the skin care behaviours corresponds to a plurality of the user actions. A duration of each of the skin care behaviours is calculated according to the image capturing time of the image information classified to each of the skin care behaviours.

The invention provides an electronic device adapted to evaluate a skin care procedure including a plurality of skin care behaviours. The electronic device includes a storage unit, an image capturing unit and a processor. The storage unit is configured to store an image capturing module, an action analysis module, a behaviour classification module and a skin care evaluation module. The image capturing unit is configured to capture an image. The processor is coupled to the storage unit and the image capturing unit, and is configured to access and execute the modules stored in the storage unit. The image capturing module sequentially obtains a plurality of image information at a plurality of image capturing time. The action analysis module analyzes a plurality of user actions corresponding to the image information, where a plurality of consecutive image information of the plurality of image information corresponds to one of the user actions. The behaviour conclusion module classifies the image information to the skin care behaviours according to the user action corresponding to each of the image information, where each of the skin care behaviours corresponds to a plurality of the user actions. The skin care evaluation module calculates a duration of each of the skin care behaviours according to the image capturing time of the image information classified to each of the skin care behaviours.

According to the above descriptions, the skin care evaluation method and the electronic device thereof provided by the invention are adapted to analyze various skin care behaviours performed by the user and durations thereof according to a plurality of images captured during a skin care process of the user. In this way, it is well evaluated whether the skin care process is adequate and indeed.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
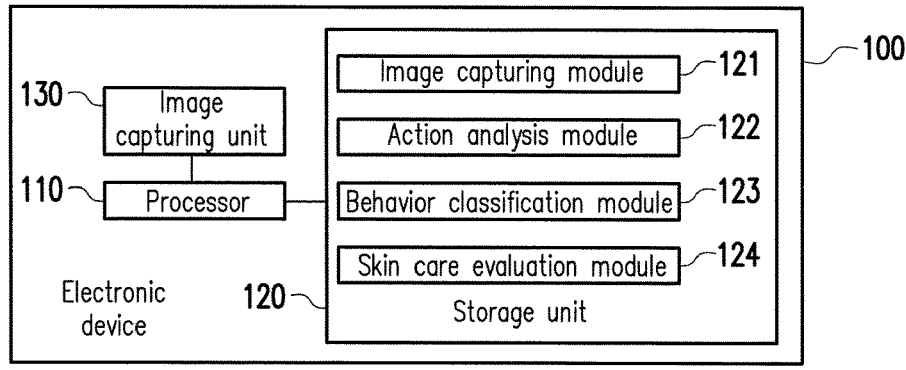
FIG. 1 is a schematic block diagram of an electronic device according to an embodiment of the invention.

FIG. 1 is a schematic block diagram of an electronic device according to an embodiment of the invention. Referring to FIG. 1, the electronic device 100 of the present embodiment at least includes a processor 110, a storage unit 120 and an image capturing unit 130, where the processor 110 is coupled to the storage unit 120 and the image capturing unit 130. The electronic device 100 of the present embodiment can be set on a mirror of a makeup table, such that when a user looks in the mirror to perform skin care, the electronic device 100 may capture and analyze action images during the skin care of the user, so as to evaluate a skin care procedure of the user, and provide related information of a skin care evaluation result by using a display (not shown) disposed behind the mirror. It should be noted that in the present embodiment, the electronic device 100 can also be an electronic product such as a smart phone, a tablet personal computer, a desktop computer, etc., or a portable mirror box combined with a portable mirror.

The processor 110 can be a central processing unit (CPU), a microprocessor, a digital signal processor, a programmable controller, an application specific integrated circuits (ASIC), a programmable logic device (PLD) or other device having a data computation function.

The storage unit 120 can be any type of a fixed or movable random access memory (RAM), a read-only memory (ROM), a flash memory, or a similar device or a combination of the above devices. In the present embodiment, the storage unit 120 is configured to record an image capturing module 121, an action analysis module 122, a behaviour classification module 123 and a skin care evaluation module 124. The above modules are, for example, computer programs stored in the storage unit 120, which can be loaded into the processor 110, and the processor 110 may accordingly execute the function of the skin care evaluation method of the invention. It should be noted that the aforementioned storage unit 120 is not limited to a single memory element, and the aforementioned modules can be separately stored in two or more memory elements of the same or different types. In other embodiments of the invention, the aforementioned modules are, for example, implemented by specific circuit structures.

The image capturing unit 130 can be a camera equipped with a charge coupled device (CCD), a complementary metal-oxide semiconductor (CMOS) device or other type of photosensing element, and is adapted to capture a plurality of images during a skin care process of the user, especially images of a face or neck area of the user.

The skin care evaluation method of the invention can be implemented by the electronic device 100 of FIG. 1. The skin care evaluation method is described below with reference to the electronic device 100 of FIG. 1. It should be noted that the skin care evaluation method is not limited to be implemented by the electronic device 100, and other electronic device or system having the corresponding capability may also be used to implement the aforementioned skin care evaluation method. Detailed steps and flow of the method are described below.

Generally, every skin care procedure may include a plurality of skin care behaviours, for example, a cleaning behaviour, a toning behaviour, a basic moisturizing behaviour, a special care behaviour, and a sun screening behaviour. In detail, the cleaning behaviour includes cleaning face and removing makeup, etc.; the toning behaviour includes replenishing skin moisture and properly toningoil secretion; the basic moisturizing behaviour includes giving skin proper moisturizer to maintain oil-water balance; the special care behaviour includes taking care of issues that needs special improvement such as dark eye circles, pimples or whitening spots, etc.; and the sun screening behaviour includes rubbing on products with sun protect factors, etc. The skin care evaluation method of the present embodiment is to evaluate a skin care procedure including a plurality of the skin care behaviours.

Figure 2:
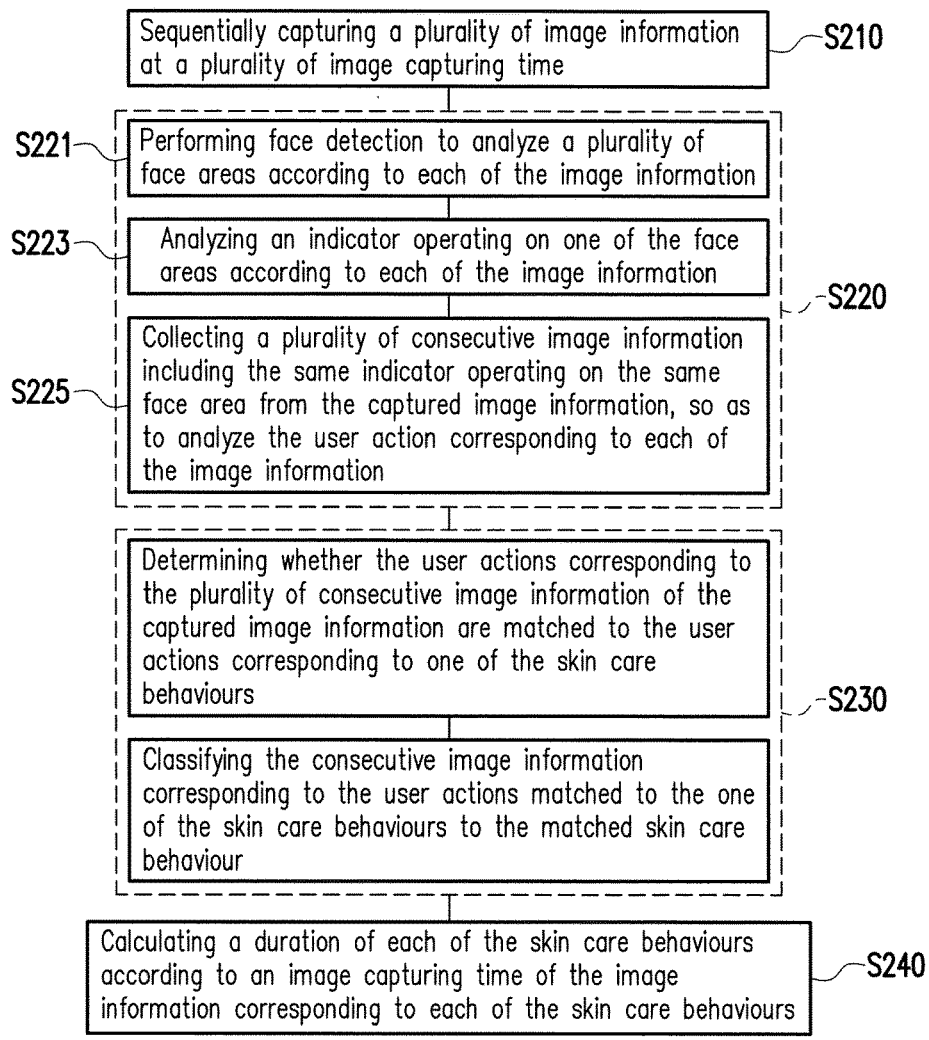
FIG. 2 is a flowchart illustrating a skin care evaluation method according to an embodiment of the invention.

FIG. 2 is a flowchart illustrating a skin care evaluation method according to an embodiment of the invention. Referring to FIG. 2, in step S210, the processor 110 executes the image capturing module 121, and the image capturing unit 130 sequentially captures a plurality of image information at a plurality of image capturing time. In the present embodiment, the processor 110, for example, uses the image capturing unit 130 to capture a plurality of images of the user at specific time intervals when the user performs the skin care procedure, and then sequentially extracts a plurality of image information from the captured images in a predetermined sampling rate. However, the sampling rate and the image capturing time are not limited by the invention. In other embodiments, the processor 110 is not limited to capture the images when the user performs the skin care procedure, but uses the image capturing unit 130 to capture a plurality of the images in specific time intervals as long as the electronic device 100 is power on, and then extracts a plurality of image information from the captured images in the required sampling rate for analysis.

Then, in step S220, the processor 110 executes the action analysis module 122 to analyze a plurality of user actions corresponding to the captured image information. In the present embodiment, the analyzed user actions include indicator information, action information and face area information. For example, a user uses a wipes the right cheek with a cotton swab. In this case, the indicator information is "the cotton swab", the action information is "wipe", and the face area information is "the right cheek". For another example, the user blankets the forehead with a makeup cotton. In this case, the indicator information is "the makeup cotton", the action information is "blanket", and the face area information is "the forehead". However, the invention is not limited thereto. In other embodiments, the user actions may also include more or less information (for example, besides the indicator information, left right hand information is also included to indicate whether the user currently uses a left hand or a right hand to operate the indicator), and those skilled in the art may define the information included in the user actions according to an actual requirement.

In order to correctly analyze the aforementioned user actions, the step S220 of the present embodiment further includes steps 221 to 225. In the step S221, the action analysis module 122 performs face detection to analyze a plurality of face areas according to each of the image information. To be specific, the action analysis module 122 performs the face detection to the image information to determine whether the image information includes at least one human face, and selects one human face from the at least one human face to serve as an analysis target. In the present embodiment, the action analysis module 122 analyzes the human face in the image information by using a plurality of (for example, but not limited to 119) feature points of human face, and analyzes a plurality of face areas such as the forehead, left and right cheeks, left and right eyes, a noise or a chin, etc., according to the feature points. In this way, the action analysis module 122 may analyze a plurality of face areas from the human face selected as the analysis target in the step S221.

Then, in step S223, the action analysis module 122 analyzes an indicator operating on one of the face areas according to each of the image information. To be specific, the action analysis module 122 performs image analysis to the image information to learn whether the face areas analyzed in the step S221 include the indicator. For example, when the user uses the cotton swab to wipe the right cheek, the action analysis module 122 may analyze the indicator to be the cotton swab, and the cotton swab operates on the right cheek.

After the captured image information is analyzed, in step S225, the action analysis module 122 collects a plurality of consecutive image information including the same indicator operating on the same face area in the captured image information, so as to analyze the user action corresponding to each of the image information. One user action can be analyzed according to a plurality of the consecutive image information.

Taking the action of "using the cotton swab to wipe the right cheek" as an example, the action of wiping is a consecutive process, so that when it is analyzed that a plurality of consecutive image information includes the cotton swab operating on the right cheek and includes a moving action of wiping, the plurality of consecutive image information corresponds to the user action of "using the cotton swab to wipe the right cheek".

Taking the action of "using the makeup cotton to blanket the forehead" as an example, although the action of blanket cannot be distinguished as consecutive different actions in the plurality of consecutive image information, a plurality of the image information is still required for determining the difference between "blanket" and "wiping", so as to determine action formation of "blanket". Therefore, in the present embodiment, when it is analyzed that a plurality of consecutive image information includes the makeup cotton operating on the forehead and a position of the makeup cotton operating on the forehead is unchanged in the plurality of consecutive image information, the action analysis module 122 determines that the plurality of consecutive image information corresponds to the user action of "using the makeup cotton to blanket the forehead".

In the present embodiment, based on the aforementioned steps S221-S225, the action analysis module 122 may analyze the user actions corresponding to the extracted image information. In an embodiment, the storage unit 120 further includes a database (for example, a following Table. 1), which records a plurality of user actions and action referential numbers thereof. The processor 110 further compares whether the user action analyzed in the step S220 is matched to the user action recorded in the database, and if yes, the user action is regarded as a qualified user action for further analysis. Conversely, it is regarded as no action.

TABLE 1

| Action referential No. | User action |
| --- | --- |
| NoAction | No action |
| Action_1 | Cotton swab wipes right cheek |
| Action_2 | Makeup cotton blanket forehead |

Then, in step S230, the processor 110 executes the behaviour classification module 123 to classify the captured image information to skin care behaviours according to the user action corresponding to each of the image information. In the present embodiment, the skin care behaviours include a cleaning behaviour, a toning behaviour, a basic moisturizing behaviour, a special care behaviour, and a sun screening behaviour, though the invention is not limited thereto, and each of the skin care behaviours is formed by connecting sequence of a plurality of user actions.

In an embodiment, regarding a first skin care behaviour, the first skin care behaviour is probably formed by a sequence of a plurality of first user actions, and the first user actions are in a restricted order. Regarding a second skin care behaviour, the second skin care behaviour is formed by a sequence of a plurality of second user actions, and the second user actions are not in a restricted order, and only the number of times and a frequency of the user actions are restricted. For example, in case of the cleaning behaviour, after the user cleans the whole face with a facial cleanser, the user rinses the face by using water, so that an order of the user actions is restricted; though in case of the base moisturizing behaviour, it is not limited to first wipe a lotion on the forehead or first wipe the same one the cheeks as long as each part of the face is adequately wiped, so that the order of the user actions is not restricted, and only the number of times and the frequency of the user actions are restricted.

In the present embodiment, the storage unit 120 includes a database, which records each of the skin care behaviours and a plurality of corresponding user actions. In order to classify the image information to the skin care behaviours, the step S230 of the present embodiment further includes steps S231-233. In the step S231, the behaviour classification module 123 determines whether the user actions corresponding to a plurality of the consecutive image information are matched to the user actions corresponding to a certain skin care behaviour recorded in the storage unit 120. Then, in step S233, the behaviour classification module 123 classifies the consecutive image information corresponding to the user actions matched to the certain skin care behaviour to the matched certain skin care behaviour.

For example, the analyzed consecutive image information probably sequentially corresponds to four user actions of "using the makeup cotton to wipe the forehead", "using the cotton swab to press the cheek", "using the makeup cotton to press the cheek", "using the makeup cotton to press the chin", and the basic moisturizing behaviour recorded in the database corresponds to three user actions of "using the makeup cotton to wipe the forehead", "using the makeup cotton to press the cheek", "using the makeup cotton to press the chin". Therefore, the user actions corresponding to the aforementioned plurality of consecutive image information and the user actions corresponding to the basic moisturizing behaviour recorded in the database only have a difference of "using the cotton swab to press the cheek", so that a matching rate is rather high. Therefore, the behaviour classification module 123 may classify the plurality of consecutive image information to the basic moisturizing behaviour in the step S233, and others are deduced by analogy. In this way, the plurality of consecutive image information of the captured plurality of image information can be classified to a certain specific skin care behaviour.

It should be noted that in the present embodiment, the behaviour classification module 123 classifies the skin care behaviour according to a matching rate threshold, where a magnitude of the matching rate threshold is not limited by the invention, which can be determined by those skilled in the art. In other embodiments, the behaviour classification module 123 may also classify the consecutive image information to the basic moisturizing behaviour when the user actions corresponding to the plurality of consecutive image information and the user actions corresponding to the skin care behaviour recorded in the database are completely matched. Moreover, in some embodiments, the captured image information may also include some image information that cannot be matched to any basic moisturizing behaviour.

Finally, in step S240, the processor 110 executes the skin care evaluation module 124 to calculate a duration of each of the skin care behaviours according to an image capturing time of the image information classified to each of the skin care behaviours.

In the present embodiment, the image capturing module 121, for example, captures 100 pieces of image information, and an image capturing time interval of two pieces of image information is 3 seconds. In the captured 100 pieces of image information, the $1^{st}$ to $10^{th}$ pieces of image information are classified to the cleaning behaviour; the $21^{st}$ to $30^{th}$ pieces of image information are classified to the toning behaviour; the $36^{th}$ to $50^{th}$ pieces of image information are classified to the basic moisturizing behaviour; the $71^{st}$ to $85^{th}$ pieces of image information are classified to the special care behaviour; the $91^{st}$ to $100^{th}$ pieces of image information are classified to the sun screening behaviour, and other image information does not correspond to any skin care behaviour. In this way, the skin care evaluation module 124 may calculate that a duration of the cleaning behaviour is about 30 seconds, a duration of the toning behaviour is about 30 seconds, a duration of the basic moisturizing behaviour is about 45 seconds, a duration of the special care behaviour is about 45 seconds, and a duration of the sun screening behaviour is about 30 seconds. It should be noted that the aforementioned embodiment is only schematic, and the invention is not limited thereto.

After the duration of each of the skin care behaviours is calculated, the processor 110 may execute the skin care evaluation module 124 to evaluate the user's skin care procedure by using the information. For example, regarding the skin care procedure of everyday of the user, the skin care evaluation module 124 may calculate an achievement rate of the skin care procedure and a total skin care time everyday, and then takes a week as a cycle to calculate a weekly skin care score and a weekly skin care achievement rate according to the achievement rate of the skin care procedure of everyday and the total skin care time in a week.

Figure 3:
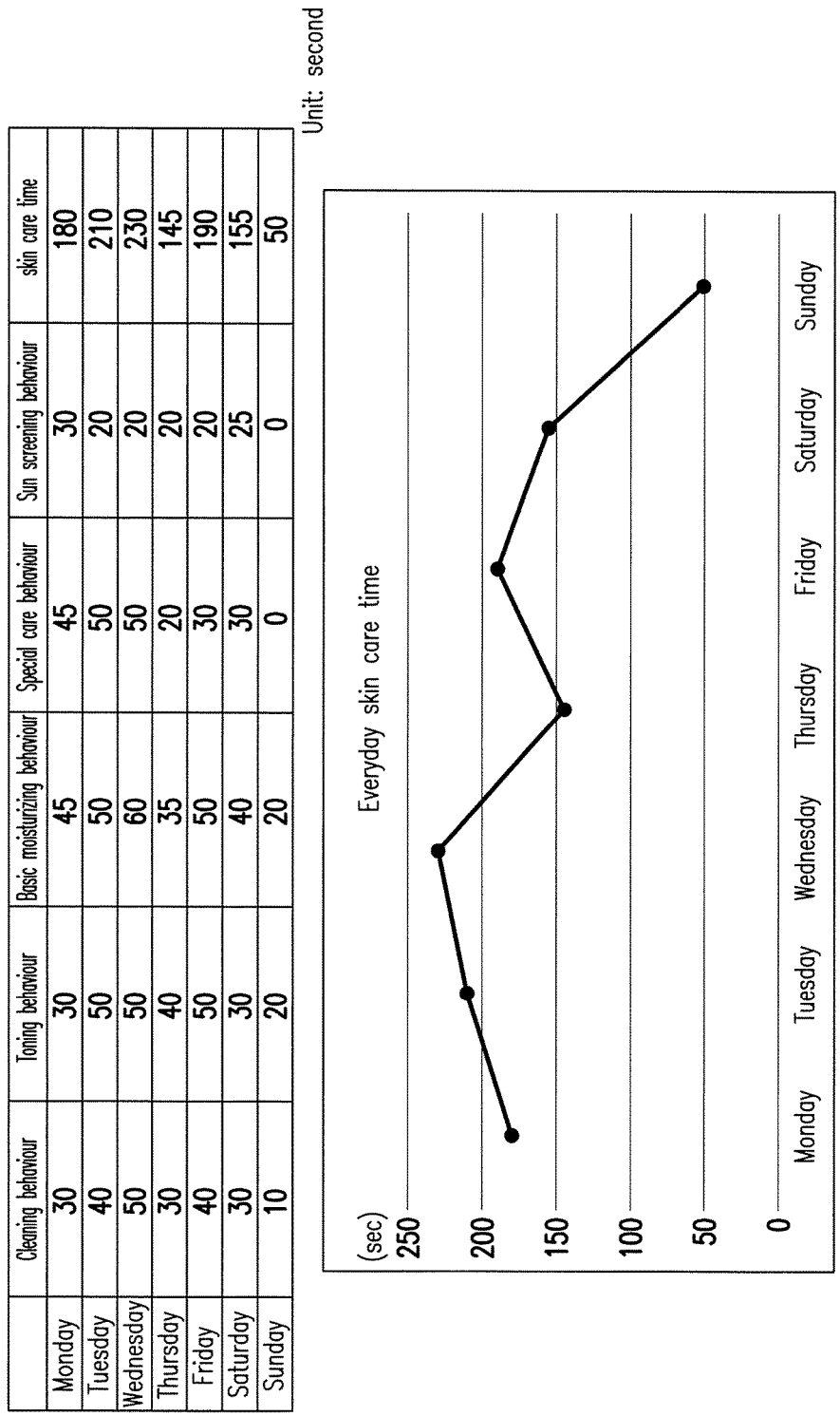
FIG. 3 is a schematic diagram illustrating duration of each skin care behaviour and total skin care time according to an embodiment of the invention.

FIG. 3 is a schematic diagram illustrating duration of each skin care behaviour and total skin care time according to an embodiment of the invention. Referring to FIG. 3, in the present embodiment, on Monday, the skin care evaluation module 124 calculates that the duration of the cleaning behaviour is about 30 seconds, the duration of the toning behaviour is about 30 seconds, the duration of the basic moisturizing behaviour is about 45 seconds, the duration of the special care behaviour is about 45 seconds, and the duration of the sun screening behaviour is about 30 seconds, so that the total skin care time on Monday is 180 seconds, and the others can be deduced by analogy. In the present embodiment, shown as the top of FIG. 3, after the processor 110 calculates the everyday total skin care time in a week, the processor 110 may display the same by using the display disposed behind the mirror.

In the present embodiment, the skin care evaluation module 124 may set a standard time and a weight value for each of the skin care behaviours, where the standard time is used for representing a time required for accomplishing the skin care behaviour. Therefore, if the duration of a specific skin care behaviour is divided by the standard time, a completion degree of the specific skin care behaviour is obtained. The completion degrees of each of the skin care behaviours multiplied by the weight values thereof are summed to obtain the achievement rate of the skin care procedure of that day.

For example, a standard time of the cleaning behaviour is, for example, 60 seconds, and a weight value thereof is, for example, 0.2; a standard time of the toning behaviour is 50 seconds, and a weight value thereof is, for example, 0.25; a standard time of the basic moisturizing behaviour is, for example, 50 seconds, and a weight value thereof is, for example, 0.25; a standard time of the special care behaviour is, for example, 60 seconds, and a weight value thereof is, for example, 0.2; and a standard time of the sun screening behaviour is, for example, 50 seconds, and a weight value thereof is, for example, 0.1. Therefore, in the present embodiment, the achievement rate of the skin care procedure on Monday is 72.5% (i.e., 0.5*0.2+0.6*0.25+0.9*0.25+0.75*0.2+1*0.1). Deduced by analogy, the skin care evaluation module 124 may calculate the achievement rate of the skin care procedure of everyday.

In the present embodiment, after the achievement rate of the skin care procedure of everyday and the total skin care time are calculated, the skin care evaluation module 124 further takes a week as a cycle to calculate a weekly skin care score according to the achievement rate of the skin care procedure of everyday and the total skin care time.

To be specific, the skin care evaluation module 124 first calculates the weekly skin care achievement rate according to a following equation (1):

$$W_R = \left[ \frac{\sum_{i=1}^{7} (Md_i \times Mw_i)}{\sum_{i=1}^{7} (Mw_i)} \right] \quad (1)$$

$W_R$ is the weekly skin care achievement rate, $Md_1$ to $Md_7$ are respectively the achievement rates of the skin care procedures from Monday to Sunday, and $Mw_1$ to $Mw_7$ are respectively the total skin care time of the skin care procedures from Monday to Sunday.

After the weekly skin care achievement rate is calculated, the skin care evaluation module 124 further obtains the weekly skin care score according to a following Table. 2.

TABLE 2

| Weekly skin care achievement rate (%) | Weekly skin care score |
|---|---|
| 91~100 | 5 |
| 85~90 | 4 |
| 80~84 | 3 |
| 70~79 | 2 |
| 60~69 | 1 |
| 0~59 | 0 |

In the present embodiment, after the skin care evaluation module 124 calculates the weekly skin care score, the weekly skin care score is further displayed on the display disposed behind the mirror, so as to facilitate the user improving the skin care estimation result.

In summary, the embodiments of the invention provide the skin care evaluation method and the electronic device thereof, which are adapted to analyze various skin care behaviours performed by the user and the durations thereof according to a plurality of images captured during the skin care process of the user. Moreover, the embodiments of the invention further calculate the achievement rate of the skin care procedure of everyday and the total skin care time according to the analyzed various skin care behaviours and the durations thereof, and then takes a week as a cycle to calculate the weekly skin care score according to the achievement rate of the skin care procedure of everyday and the total skin care time. In this way, the user may well estimate whether the performed skin care procedure is adequate and indeed.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A skin care evaluation method for evaluating a skin care procedure comprising a plurality of skin care behaviours, applicable to an electronic device in which at least one user action corresponding to each skin behaviour is recorded, the skin care evaluation method comprising:

sequentially capturing a plurality of images;
performing a face detection on the images to analyze a
  plurality of face areas in each image, and performing an image analysis on the images to determine an indicator operating on one of the face areas in each image and a type of the indicator;

determining a plurality of user actions in the images based on the type of the indicator and the face area on which the indicator operates in the images;

determining at least one of the skin care behaviours in the images by matching at least one of the user actions in the images to one of the skin care behaviours;

calculating a duration of each skin care behaviour in the images based on image capturing times of the images; and setting a standard time and a weight value for each skin care behaviour and calculating an achievement rate of the skin care procedure based on the duration, the standard time and the weight value of each skin care behaviour.

2. The skin care evaluation method as claimed in claim 1, wherein the user action comprises an indicator information, an action information and a face area information.

3. An electronic device for evaluating a skin care procedure comprising a plurality of skin care behaviours, in which at least one user action corresponding to each skin behaviour is recorded, the electronic device comprising:

a storage unit, configured to store a plurality of modules;

an image capturing unit, configured to capture an image; and a processor, coupled to the storage unit and the image capturing unit, and configured to access and execute the modules stored in the storage unit, the modules comprise:

an image capturing module, sequentially obtaining a plurality of images;

an action analysis module, performing a face detection on the images to analyze a plurality of face areas in each image, performing an image analysis on the images to determine an indicator operating on one of the face areas in each image and a type of the indicator and determining a plurality of user actions in the images based on the type of the indicator and the face area on which the indicator operates in the images;

a behaviour classification module, determining at least one of the skin care behaviours in the images by matching at least one of the user actions in the images to one of the skin care behaviours; and a skin care evaluation module, calculating a duration of each skin care behaviour in the images based on image capturing times of the images and setting a standard time and a weight value for each skin care behaviour and calculating an achievement rate of the skin care procedure based on the duration, the standard time and the weight value of each skin care behaviour.

4. The electronic device as claimed in claim 3, wherein the user action comprises an indicator information, an action information and a face area information.

* * * * *